United States Patent [19]

Anello

[11] 4,367,349

[45] Jan. 4, 1983

[54] LIQUID PHASE SYNTHESIS OF HEXAFLUOROISOBUTYLENE

[75] Inventor: Louis G. Anello, Hamburg, N.Y.

[73] Assignee: Allied Corporation, Morris Township, Morris County, N.J.

[21] Appl. No.: 275,010

[22] Filed: Jun. 18, 1981

[51] Int. Cl.³ .............................................. C07C 17/00
[52] U.S. Cl. ........................................ 570/140; 549/89
[58] Field of Search ................... 570/142, 140; 549/89

[56] References Cited

U.S. PATENT DOCUMENTS 3,894,097  7/1975  Vanderkooi et al. ................ 570/142
4,244,891  1/1981  Van Der Puy et al. ............ 570/140

*Primary Examiner*—Charles F. Warren
*Assistant Examiner*—Joseph A. Boska
*Attorney, Agent, or Firm*—Thomas D. Hoffman; Jay P. Friedenson

[57] ABSTRACT

The process for preparing hexafluoroisobutylene is disclosed which comprises reacting, in the liquid phase, formaldehyde or a formaldehyde-generating compound with hexafluorothioacetone dimer in an aprotic solvent containing at least a catalytic amount of an alkali metal fluoride or a sulfonic acid having general formula $RSO_3H$ is disclosed. The preferred aprotic solvents are dimethylformamide, N-methyl pyrrolidone and dimethyl sulfoxide. The preferred alkali metal fluoride is KF; the preferred sulfonic acids are $CH_3SO_3H$ and p-$CH_3C_6H_4SO_3H$. The production of hexafluoroisobutylene by contacting hexafluoropropene with elemental sulfur and a catalytic amount of an alkali metal fluoride such as KF in an aprotic solvent such as dimethyl sulfoxide or N-methyl pyrrolidone at a temperature of between about 40° and about 70° C. for a time sufficient to produce hexafluorothioacetone dimer combined with contacting said dimer in said aprotic solvent containing said alkali metal fluoride at a temperature between about 100° C. and 150° C. for a time sufficient to produce an effluent stream containing hexafluoroisobutylene which is recovered therefrom is also disclosed.

20 Claims, No Drawings

LIQUID PHASE SYNTHESIS OF HEXAFLUOROISOBUTYLENE

FIELD OF THE INVENTION

This invention relates to a process for the preparation of hexafluoroisobutylene by reacting, in the liquid phase, formaldehyde or a formaldehyde-generating compound with hexafluorothioacetone dimer in an aprotic solvent containing a catalytic amount of an alkali metal fluoride or a sulfonic acid. The invention also relates to a process for preparation of hexafluoroisobutylene by contacting, at low temperatures, hexafluoropropene with elemental sulfur and alkali metal fluoride in an aprotic solvent for a time sufficient to produce hexafluorothioacetone dimer combined with contacting the dimer, at elevated temperatures, with formaldehyde or a formaldehyde-generating agent in an aprotic solvent containing alkali metal fluoride or sulfonic acid to produce hexafluoroisobutylene.

BACKGROUND OF THE INVENTION

Hexafluoroisobutylene is a known compound which is known to be useful for a variety of purposes such as, for example, a comonomer which forms polymers of exceptional thermal, chemical and mechanical properties with other comonomers such as vinylidene fluoride. The preparation of such copolymers is described in U.S. Pat. No. 3,706,723 to Chandrasekeran et al., issued Dec. 19, 1972. Hexafluoroisobutylene has been previously prepared by methods which include the reaction of hexafluoroacetone with ketene (U.S. Pat. No. 3,894,097 to N. Vanderkooi), the reaction of hexafluorothioacetone with ketene or a ketene-generating compound (U.S. Pat. No. 4,244,891 to Van Der Puy et al.), the reaction of antimony trifluorodichloride with a chlorofluoroisobutylene [R. N. Hazeldine, *J. Chem. Soc.*, 3565 (1953)] and the dehydration of hexafluoro-2-methyl-2-propanol with phosphorus pentachloride [M. H. Kaufman et al., *J. Org. Chem.* 31, 3090 (1966)] or with sulfur tetrafluoride (E. E. Gilbert et al. in U.S. Pat. No. 3,656,786). These preparations and others suffer from one or more disadvantages from a commercial standpoint. For example, although the preparation involving hexafluoroacetone is a high-yield process, hexafluoroacetone represents a starting material of high cost and limited availability. The chlorofluoroisobutylene route involves several steps including a slow dehydrochlorination step, while the dehydration of the fluorinated tertiary butyl alcohol requires excessively long reaction times or expensive reagents. The reaction of hexafluorothioacetone with ketene operates in the gas phase at elevated temperature (300°–800° C.) and requires special reactors.

It is accordingly an object of the invention to provide a new route to hexafluoroisobutylene which utilizes cheaper and more readily accessible starting materials and which operates at milder reaction conditions in the liquid phase.

Other objects and advantages of the invention will become apparent from the following description.

SUMMARY OF THE INVENTION

It has been found that hexafluoroisobutylene may be conveniently prepared by reacting, in the liquid phase, hexafluorothioacetone dimer with formaldehyde or a formaldehyde-generating compound in an aprotic solvent containing at least a catalytic amount of an alkali metal fluoride or a sulfonic acid having the formula $RSO_3H$ wherein R is an organic radical selected from the group consisting of straight and branched chain alkyl groups having one to fourteen carbons, aryl groups having six to ten carbons, monoalkylaryl groups herein alkyl is a straight or branched chain carbon group having one to fourteen carbon atoms and wherein aryl is an aromatic group containing six to ten carbon atoms, and dialkylaryl wherein each alkyl group is independently a straight or branched chain organic group having one to fourteen carbon atoms and wherein the aryl is an aromatic group containing six to ten carbon atoms.

The present invention also provides a process for the preparation of hexafluoroisobutylene which comprises:

(a) contacting hexafluoropropene with elemental sulfur and a catalytic amount of an alkali metal fluoride in an aprotic solvent selected from the group consisting of dimethylacetamide, dimethylformamide, dimethyl sulfoxide and N-methyl pyrrolidone while maintaining the temperature of the contacting between about 40° and 70° C. for a time sufficient to produce hexafluorothioacetone dimer;

(b) contacting each mole of said hexafluorothioacetone dimer in said aprotic solvent containing said alkali metal fluoride with at least two moles of formaldehyde or formaldehyde-generating compound at a temperature between about 100° and 150° C. and optionally adding additional alkali metal flouride;

(c) maintaining the temperature of the contacting between about 100° and 150° C. for a time sufficient to produce hexafluoroisobutylene in an effluent stream; and (d) recovering hexafluoroisobutylene from said effluent stream.

DETAILED DESCRIPTION OF THE INVENTION AND OF THE PREFERRED EMBODIMENTS

The formaldehyde reactant may be gaseous formaldehyde or a formaldehyde-generating compound which will generate formaldehyde under the reaction conditions of the present invention and make formaldehyde available to react with hexafluorothioacetone dimer. Exemplary of such formaldehyde-generating compounds found useful in the process of the present invention are paraformaldehyde, trioxane (α-trioxy-methylene), and mixtures thereof. The preferred formaldehyde-generating compounds are paraformaldehyde and trioxane.

Hexafluorothioacetone dimer is prepared by reaction of hexafluoropropene with sulfur and alkali metal fluoride such as KF in tetramethylene sulfone or nitrobenzene at a temperature of 120° to 150° C. in an autoclave under elevated pressure (B. L. Dyatkin et al., in *Tetrahedron*, 29, 2759–2760 (1973)).

The preparation of hexafluorothioacetone dimer by reaction of hexafluoropropene with elemental sulfur and alkali metal fluoride such as KF, in an aprotic solvent such as dimethylformamide under substantially atmospheric pressure and at temperatures between about 25° and 100° C. is disclosed in copending U.S. patent application Ser. No. 216,035 filed on Dec. 15, 1980 by L. G. Anello et al.

Exemplary of the aprotic solvents found useful in the process of the present invention are dimethylacetamide, dimethylformamide, dimethyl sulfoxide and N-methyl pyrrolidone and mixtures thereof. Dimethylformamide, N-methyl pyrrolidone and dimethyl sulfoxide are preferred aprotic solvents. Dimethyl sulfoxide and N-methyl pyrrolidone are more preferred.

Exemplary of the catalyst found useful in the process of the present invention are alkali metal fluorides selected from the group consisting of LiF, NaF, KF and CsF, and organic sulfonic acids having formula $RSO_3H$ wherein R is an organic radical selected from the group consisting of linear and branched chain alkyl groups having one to fourteen carbon atoms, aryl groups having six to ten carbon atoms, monoalkylaryl groups wherein alkyl is a straight or branched chain carbon group having one to fourteen carbon atoms and wherein aryl is an aromatic group containing six to ten carbon atoms, and dialkyl aryl group wherein each alkyl group is independently a straight or branched chain organic group having one to fourteen carbon atoms, and wherein aryl is an aromatic group containing six to ten carbon atoms. The preferred alkali metal fluoride is KF. The preferred organic sulfonic acids are $CH_3SO_3H$ and $p-CH_3C_6H_4SO_3H$. While hydrated forms of the organic sulfonic acid may be used, it is preferred to use the anhydrous forms thereof.

Reaction temperatures are not critical, but generally the reaction should be conducted at temperatures from about 25° C. up to the boiling point of the aprotic solvent. The preferred temperature range is from about 100° C. to about 150° C. at atmospheric pressure. For temperatures above about 150° C., super atmospheric pressure should be employed.

Reaction times for the present invention are not critical. Reaction times of about 5-8 hours for reaction temperatures in the range of from about 100° to 150° C. are adequate to achieve the objects and advantages of the present invention.

The molar ratio of alkali metal fluoride or organic sulfonic acid having formula $RSO_3H$ catalyst to hexafluorothioacetone dimer is not critical. The molar ratio of catalyst to hexafluorothioacetone dimer is preferably from about 0.06:1 to 5:1, more preferably from about 0.06:1 to 1:1. Molar ratios in the more preferred range are adequate for the preparation of hexafluoroisobutylene. Only economic considerations would preclude employing higher molar ratios.

The molar ratio of hexafluorothioacetone dimer to formaldehyde or formaldehyde-generating compound is not critical. There is no particular advantage in having the more expensive hexafluorothioacetone dimer in moderate excess. However, it is advantageous to have a slight excess of the less expensive formaldehyde or formaldehyde-generating compound to effect complete conversion of the hexafluorothioacetone dimer to hexafluoroisobutylene. Accordingly, molar ratio of hexafluorothioacetone dimer to formaldehyde or formaldehyde-generating compounds such as paraformaldehyde is conveniently, for economic reasons, at least about 1:2, and preferably is about 1:2 to about 1:6. The more preferred molar ratio of hexafluorothioacetone dimer to formaldehyde of formaldehyde-generating compound is about 1:2 to about 1:4.

The concentration of aprotic solvent such as dimethylformamide to hexafluorothioacetone dimer is not critical, but sufficient aprotic solvent should be present to permit stirring and solution of the reaction mixture of hexafluorothioacetone dimer, formaldehyde or formaldehyde-generating compound and catalyst such as KF, $CH_3SO_3H$ or $p-CH_3C_6H_4SO_3H$. It is preferred that 100 mL of aprotic solvent be present for each 100 mL of hexafluorothioacetone dimer present.

In an illustrative typical embodiment of the present invention, hexafluorothioacetone dimer and paraformaldehyde in dimethylformamide containing anhydrous KF are slowly heated with agitation to the reflux temperature. Refluxing may begin at 110° C. (bp. of hexafluorothioacetone dimer) but heating is continued until the temperature of the reaction reaches 150° C. (b.p. of dimethylformamide). During the heating period, hexafluoroisobutylene distills out of the reaction flask and condenses in a cold trap. Hexafluoroacetone, which also forms, may distill out and be co-mixed with the desired hexafluoroisobutylene. Hexafluoroisobutylene is conveniently purified via fractional distillation and is recovered by trapping the distillate containing same at sufficiently high pressure and sufficiently low temperature to condense hexafluoroisobutylene. Analysis for purity is conveniently performed on standard gas chromatographic equipment.

In a preferred embodiment of the present invention, hexafluoroisobutylene is prepared in a single reaction vessel directly without isolating hexafluorothioacetone dimer, by reacting hexafluoropropene with elemental sulfur and a catalytic amount of an alkali metal fluoride such as KF in an aprotic solvent such as dimethylformamide, dimethyl sulfoxide or N-methyl pyrrolidone at a temperature between about 40° C. and about 70° C. for a time sufficient to produce hexafluoroacetone dimer. At least about 2 moles of formaldehyde or formaldehyde-generating compound is added to each mole of hexafluorothioacetone dimer produced and the temperature is raised to between about 100° C. and about 150° C. Optionally, additional alkali metal fluoride such as KF is added. The reaction is maintained at a temperature of between about 100° C. and 150° C. for a time sufficient to produce an effluent stream containing hexafluoroisobutylene which is collected in a cold trap. The hexafluoroisobutylene is recovered conveniently via fractional distillation at reduced pressure.

While an alkali metal fluoride such as KF or sulfonic acid having general formula $RSO_3H$ is a catalyst for reactions of hexafluorothioacetone with formaldehyde or formaldehyde-generating compound to produce hexafluoroisobutylene, an alkali metal fluoride such as KF, but not sulfonic acids having general formula $RSO_3H$, is an effective catalyst for the reaction of hexafluoropropene with elemental sulfur in an aprotic solvent. Accordingly, the one vessel preparation of hexafluoroisobutylene from hexafluoropropene is conveniently catalyzed by an alkali metal fluoride, preferably KF.

The following examples illustrate and describe but do not limit the scope of the present invention which is set forth in the appended claims.

EXAMPLE 1

Into a 250 mL, 3 neck flask fitted with thermometer, stirrer, and a $-20°$ C. cooled condenser connected to a dry ice-acetone cooled trap was charged 50 g (0.137 mole) of

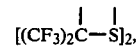

5 g (0.086 mole) KF, 25 g (0.83 mole) of paraformaldehyde powder and 140 mL of dimethylformamide. The mixture was heated to 110° C. (reflux) and then slowly heated to 150° C. over a period of 6 hours. The effluent gases from the reaction vessel were collected in the dry ice-acetone trap. The trap yielded 36.5 g crude product, which by GC analysis indicated that 11.2 g (0.067 mole) was hexafluoroacetone (CF₃COCF₃) and 11.6 g (0.071 mole) was hexafluoroisobutylene. The yields were respectively 24.5% and 26.2% based on starting hexafluorothioacetone dimer.

EXAMPLE 2

Following the procedure of Example 1, 100 g (0.272 mole) of

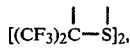

3 g (0.051 mole) of KF, 36 g (1.20 mole) of paraformaldehyde and 150 mL of dimethylacetamide were heated from 100° C. to 150° C. over a period of 3 hours. The cold trap yielded 53.3 g of crude product, which by GC analysis indicated that 12.4 g (0.074 mole) was hexafluoroacetone and 26.7 g (0.163 mole) was hexafluoroisobutylene and 7 g (0.11 mole) of acetyl fluoride. The yields of hexafluoroacetone and hexafluoroisobutylene were 13.4% and 29.6%, respectively, based on starting hexafluorothioacetone dimer.

EXAMPLE 3

Following the procedure of Example 1, 25 g (0.83 mole) of paraformaldehyde, 3 g p-toluenesulfonic acid hydrate and 120 mL of dimethylformamide were heated to 105° to 110° C. for 1 hour to remove moisture. Fifty grams (0.137 mole) of

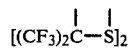

were then charged and the mixture heated from 105° to 150° C. over a 4 hour period. The cold trap yielded 22.5 g of crude product which by GC analysis indicated that 14.6 g (0.09 mole) was hexafluoroacetone and 4.5 g (0.03 mole) was hexafluoroisobutylene. The yields of hexafluoroacetone and hexafluoroisobutylene were 32% and 10% respectively based on starting hexafluorothioacetone dimer.

EXAMPLE 4

Following the procedure of Example 1, 50 g (0.137 mole) of

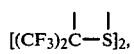

2.5 g of anhydrous KF, 25 g (0.83 mole) of paraformaldehyde and 100 mL of dimethyl sulfoxide were heated from 85° to 150° C. over a 5 hour period. The cold trap yielded 42 g of crude product, which by GC analysis indicated that 10 g (0.33 mole) was formaldehyde, 15.5 g (0.094 mole) was hexafluoroisobutylene and 15.6 g (0.254 mole) was dimethyl sulfide. The yield of hexafluoroisobutylene was 34.2% based on starting hexafluorothioacetone dimer.

EXAMPLE 5

Following the procedure of Example 1, 100 g (0.274 mole)

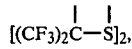

3.5 g anhydrous KF, 60 g (2.02 mole) trioxane (α-trioxymethylene), 50 mL dimethylformamide and 100 mL dimethylacetamide were heated from 100° C. to 143° C. over a 25 hour period. The cold trap yielded 29.4 g crude product which on GC analysis indicated that 15 g (0.09 mole) was CF₃COCF₃, 4.4 g (0.027 mole) was (CF₃)₂C=CH₂ and 5.0 g (0.023 mole) was (CF₃)₃CH. The yields of hexafluoroacetone and hexafluoroisobutylene were 16.4% and 4.9% respectively based on starting hexafluorothioacetone dimer.

EXAMPLE 6

Following the procedure of Example 1, 50 g (0.137 mole) of

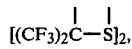

2.5 g anhydrous KF, 25 g (0.83 mole) of paraformaldehyde and 100 mL of N-methyl pyrrolidone were heated to 90° C. to 140° C. over a 7 hour period. The cold trap yielded 25 g crude product which on GC analysis indicated that 21 g (0.128 mole) was hexafluoroisobutylene. The yield of hexafluoroisobutylene was 48% based on starting hexafluorothioacetone dimer.

EXAMPLE 7

Following the procedure of Example 1, 50 g (0.13 mole) of

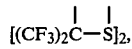

3 g of CH₃SO₃H, 15 g (0.50 mole) of paraformaldehyde, and 100 mL of N-methyl pyrrolidone were heated from 100° C. to 145° C. for a 5 hour period. There was recovered 20 g crude product in the cold trap which on GC analysis indicated that 10 g (0.061 mole) was hexafluoroisobutylene. The yield was 23% based on starting hexafluorothioacetone dimer.

EXAMPLES 8–11

In the following examples, the process of Example 1 is repeated in same apparatus excepting that the catalyst and the source of formaldehyde are varied as indicated in the following Table.

TABLE 1

| Example | Catalyst | Source of Formaldehyde |
|---|---|---|
| 8 | CH₃SO₃H | CH₂O |
| 9 | CH₃SO₃H | α-trioxane |
| 10 | p-CH₃C₆H₄SO₃H | α-trioxane |
| 11 | p-C₁₂H₂₅C₆H₄SO₃H | α-trioxane |

The molar ratio of catalyst to hexafluorothioacetone dimer is 0.06:1. The reaction temperature is 100° to 125° C.

EXAMPLES 12–16

In the following examples, the process of Example 4 is repeated in the apparatus of Example 1, excepting that the catalyst and source of formaldehyde are varied as indicated in the following Table.

TABLE 2

| Example | Catalyst | Source of Formaldehyde |
|---|---|---|
| 12 | $CH_3SO_3H$ | $CH_2O$ |
| 13 | $CH_3SO_3H$ | α-trioxane |
| 14 | p-$CH_3C_6H_4SO_3H$ | $CH_2O$ |
| 15 | p-$CH_3C_6H_4SO_3H$ | paraformaldehyde |
| 16 | p-$CH_3C_6H_4SO_3H$ | α-trioxane |

The molar ratio of catalyst to hexafluorothioacetone dimer is 0.06:1. The reaction temperature is 85° C. to 150° C.

EXAMPLE 17

Into a 500 mL 3-neck flask equipped with a thermometer, mechanical stirrer, gas inlet tube and a water-cooled condenser was charged 48 g (1.50 moles) sulfur, 87.0 g (1.50 moles) of anhydrous potassium fluoride and 200 mL dimethylformamide. The mixture was heated to 40°–45° C. and 218 g (1.45 moles) hexafluoropropene added during 2¼ hours. An additional 16 g (0.50 mole) sulfur was added and 88 g (0.58 mole) of hexafluoropropene added during a 2 hour period at 55° C. Total sulfur reacted was 64 g (2.0 moles) and total hexafluoropropene added was 306 g (2.04 moles). The contents of the flask were poured into a separatory funnel and the lower layer, 353.5 g, was phase separated from the upper layer. The lower layer was chilled to −10° C. and dimethylformamide solvent separated from the crystallized hexafluorothioacetone dimer. The recovered dimer was fractionally distilled to give 285 g (0.78 mole) of dimer for a 76% conversion and yield.

EXAMPLE 18

The procedure of Example 17 is followed excepting that hexafluorothioacetone dimer is not isolated. Paraformaldehyde (47 g, 1.56 mole) is added to the flask containing dimer. Additional KF is added and the temperature is raised to 100° to 150° C. The hexafluoroisobutylene is recovered from a dry ice-acetone trap.

EXAMPLES 19–21

The procedure of Example 18 is followed excepting that the aprotic solvent is dimethylacetamide in Example 19, dimethyl sulfoxide in Example 20 and N-methyl pyrrolidone in Example 21.

What is claimed is:

1. A process for the preparation of hexafluoroisobutylene which comprises reacting, in the liquid phase, hexafluorothioacetone dimer with formaldehyde or a formaldehyde-generating compound in an aprotic solvent containing at least a catalytic amount of an alkali metal fluoride or a sulfonic acid having the formula $RSO_3H$ wherein R is an organic radical selected from the group consisting of straight and branched chain alkyl groups having one to fourteen carbon atoms, aryl groups having six to ten carbon atoms, monoalkylaryl groups wherein alkyl is a straight or branched chain carbon group having one to fourteen carbon atoms and wherein aryl is an aromatic group containing six to ten carbon atoms, and dialkylaryl wherein each alkyl group is independently a straight or branched chain organic group having one to fourteen carbon atoms and wherein aryl is an aromatic group containing six to ten carbon atoms.

2. The process of claim 1 wherein hexafluorothioacetone dimer is reacted with formaldehyde.

3. The process of claim 1 wherein hexafluorothioacetone dimer is reacted with paraformaldehyde.

4. The process of claim 1 wherein hexafluorothioacetone dimer is reacted with α-trioxane.

5. The process of claim 2, 3 or 4 wherein the aprotic solvent is dimethylformamide.

6. The process of claim 2, 3 or 4 wherein the aprotic solvent is dimethyl sulfoxide.

7. The process of claim 2, 3 or 4 wherein the aprotic solvent is N-methyl pyrrolidone.

8. The process of claim 2, 3 or 4 wherein the aprotic solvent is dimethylformamide which contains at least about 0.06 moles of KF per about one mole of hexafluorothioacetone dimer.

9. The process of claim 2, 3 or 4 wherein the aprotic solvent is dimethyl sulfoxide which contains at least about 0.06 moles of $CH_3SO_3H$ per about one mole of hexafluorothioacetone dimer.

10. The process of claim 2, 3 or 4 wherein the aprotic solvent is dimethylformamide which contains at least about 0.06 moles of $CH_3SO_3H$ per about one mole of hexafluorothioacetone dimer.

11. The process of claim 2, 3 or 4 wherein the aprotic solvent is dimethylformamide which contains at least about 0.06 moles of p-$CH_3C_6H_4SO_3H$ per about one mole of hexafluorothioacetone dimer.

12. The process of claim 2, 3 or 4 wherein the aprotic solvent is dimethyl sulfoxide which contains at least about 0.06 moles of KF per about one mole of hexafluorothioacetone dimer.

13. The process of claim 2, 3 or 4 wherein the aprotic solvent is dimethyl sulfoxide which contains at least about 0.06 moles of p-$CH_3C_6H_4SO_3H$ per one mole of hexafluorothioacetone dimer.

14. The process of claim 2, 3 or 4 wherein the molar ratio of hexafluorothioacetone dimer:formaldehyde or formaldehyde-generating compound is about 1:2 to about 1:4.

15. A process for the preparation of hexafluoroisobutylene which comprises:
  (a) contacting hexafluoropropene with elemental sulfur and a catalytic amount of an alkali metal fluoride in an aprotic solvent selected from the group consisting of dimethylacetamide, dimethylformamide, dimethyl sulfoxide and N-methyl pyrrolidone while maintaining the temperature of the contacting between about 40° and 70° C. for a time sufficient to produce hexafluorothioacetone dimer;
  (b) contacting each mole of said hexafluorothioacetone dimer in said aprotic solvent containing said alkali metal fluoride with at least two moles of formaldehyde or formaldehyde-generating compound at a temperature between about 100° and 150° C. and optionally adding additional alkali metal fluoride;
  (c) maintaining the temperature of the contacting between about 100° and 150° C. for a time sufficient to produce hexafluoroisobutylene in an effluent stream; and
  (d) recovering hexafluoroisobutylene from said effluent stream.

16. The process of claim 15 wherein the alkali metal fluoride is KF which is added only in step (a).

17. The process of claim 15 wherein the alkali metal fluoride is KF which is added in step (a) and step (b).

18. The process of claim 16 wherein the aprotic solvent is dimethylformamide.

19. The process of claim 16 wherein the aprotic solvent is dimethyl sulfoxide.

20. The process of claim 16 wherein the aprotic solvent is N-methyl pyrrolidone.

* * * * *